United States Patent
Schurr (10) Patent No.: US 11,882,894 B2
(45) Date of Patent: Jan. 30, 2024

(54) UPPER GARMENT WORN DURING OVERHEAD WELDING

(71) Applicant: UP IN SMOKE WELDING APPAREL INC., Calgary (CA)

(72) Inventor: Mackenzie D. Schurr, Calgary (CA)

(73) Assignee: UP IN SMOKE WELDING APPAREL INC., Calgary (CA)

( * ) Notice: Subject to any disclaimer, the term of this patent is extended or adjusted under 35 U.S.C. 154(b) by 0 days.

(21) Appl. No.: 17/824,652

(22) Filed: May 25, 2022

(65) Prior Publication Data
US 2022/0279889 A1 Sep. 8, 2022

Related U.S. Application Data (63) Continuation of application No. 14/682,250, filed on Apr. 9, 2015, now Pat. No. 11,350,690.

(51) Int. Cl.
*A42B 3/22* (2006.01)
*A41D 13/00* (2006.01)
*A61F 9/06* (2006.01)

(52) U.S. Cl.
CPC .............. *A42B 3/225* (2013.01); *A41D 13/00* (2013.01); *A41D 2200/20* (2013.01); *A41D 2600/202* (2013.01); *A61F 9/06* (2013.01)

(58) Field of Classification Search
CPC ........... A42B 3/225; A61F 9/06; A41D 13/00; A41D 2200/20; A41D 2600/202
See application file for complete search history.

(56) References Cited

U.S. PATENT DOCUMENTS

| | | | |
|---|---|---|---|
| 2,036,609 A | 4/1936 | Rosen | |
| 2,388,234 A | 11/1945 | Abel | |
| 2,507,322 A * | 5/1950 | Smith | A41D 3/00 D2/831 |
| 3,691,564 A * | 9/1972 | La Marre | A41D 13/00 2/81 |
| 3,761,962 A | 10/1973 | Myers | |

(Continued)

FOREIGN PATENT DOCUMENTS

CN 103564734 2/2014

OTHER PUBLICATIONS

"2013 new winter horn button fur sherpa jackets and long Slim Suede Women Bonding Fux Fur Jacket Warm Clothes/Coats," Shop 131998 Store at AliExpress, 2013, retrieved from https://www.aliexpress.comm/item/1494966243.html, 10 pages.

(Continued)

*Primary Examiner* — Bao-Thieu L Nguyen
(74) *Attorney, Agent, or Firm* — Sheridan Ross P.C.

(57) ABSTRACT

Described is an upper garment worn by welders while welding overhead, which is made of a breathable fabric and leather. The garment has a hood comprising leather attached to the neckline of the garment body, at least one leather sleeve, and leather on one shoulder and an upper front portion and an upper back portion of the garment that is contiguous with the at least one leather sleeve. The hood may be partially or completely made of leather, and the other sleeve may be leather. The strategic placement of leather on the garment improves the garment's durability, minimizes burns on the wearer from sparks and spatter, and protects the garment from the environment.

16 Claims, 5 Drawing Sheets

(56) References Cited

U.S. PATENT DOCUMENTS

| | | | |
|---|---|---|---|
| 4,017,908 A * | 4/1977 | Murnane | A41D 13/0125 2/114 |
| 4,513,451 A | 4/1985 | Brown | |
| 4,608,715 A | 9/1986 | Miller et al. | |
| 4,706,304 A * | 11/1987 | Jones | A41D 27/10 2/91 |
| 4,722,099 A | 2/1988 | Kratz | |
| 5,210,877 A * | 5/1993 | Newman | A41D 1/067 2/243.1 |
| 5,507,042 A | 4/1996 | Van Der Sleesen | |
| 5,628,065 A * | 5/1997 | Austin | A42B 1/048 2/5 |
| 5,704,064 A | 1/1998 | Van Der Sleesen | |
| 5,752,277 A | 5/1998 | Van Der Sleesen | |
| 5,860,163 A * | 1/1999 | Aldridge | A41D 31/065 2/81 |
| 5,920,903 A * | 7/1999 | Koehntop | A41D 13/00 2/69 |
| 5,983,409 A * | 11/1999 | Aldridge | A41D 13/00 2/81 |
| 6,427,242 B1 | 8/2002 | Bush et al. | |
| 6,430,754 B1 * | 8/2002 | Taylor | A41D 31/085 2/87 |
| 6,499,141 B1 * | 12/2002 | Egnew | F41H 3/00 2/108 |
| 6,675,394 B2 * | 1/2004 | Egnew | A41D 13/00 2/227 |
| 6,868,557 B1 | 3/2005 | Van Der Sleesen | |
| 9,655,384 B2 * | 5/2017 | Roscoe | A41D 31/185 |
| 9,731,152 B2 * | 8/2017 | Swartz, IV | A41D 13/00 |
| 11,350,690 B2 * | 6/2022 | Schurr | A41D 13/00 |
| 2003/0084498 A1 * | 5/2003 | Egnew | F41H 3/00 2/94 |
| 2003/0140404 A1 | 7/2003 | Golde | |
| 2005/0204449 A1 | 9/2005 | Baron et al. | |
| 2005/0251900 A1 | 11/2005 | Harlacker | |
| 2006/0028430 A1 | 2/2006 | Harary et al. | |
| 2006/0075537 A1 | 4/2006 | Tsai | |
| 2007/0094763 A1 * | 5/2007 | Silver | A41D 27/28 2/69 |
| 2007/0245443 A1 | 10/2007 | Vereen | |
| 2008/0098503 A1 * | 5/2008 | Swartz | A41D 13/04 2/81 |
| 2010/0199404 A1 | 8/2010 | Garza | |
| 2010/0212061 A1 | 8/2010 | Luciano | |
| 2013/0276201 A1 | 10/2013 | Pezzimenti | |
| 2013/0283511 A1 * | 10/2013 | Diamond | A63B 71/12 2/455 |
| 2014/0033393 A1 | 2/2014 | Best | |
| 2015/0201693 A1 | 7/2015 | Donner et al. | |
| 2015/0327612 A1 | 11/2015 | Bublitz | |
| 2015/0374050 A1 | 12/2015 | Farron et al. | |
| 2016/0015104 A1 | 1/2016 | Edwards et al. | |
| 2016/0295939 A1 | 10/2016 | Mazzarolo et al. | |
| 2016/0309812 A1 * | 10/2016 | Scheid | A41D 15/00 |
| 2017/0188640 A1 * | 7/2017 | Schlager | A41D 13/008 |
| 2017/0332442 A1 | 11/2017 | Strecker | |
| 2019/0027889 A1 | 1/2019 | Song et al. | |
| 2020/0069980 A1 * | 3/2020 | Sonntag | A41D 31/085 |
| 2022/0184428 A1 * | 6/2022 | Tew | A41D 27/02 |

OTHER PUBLICATIONS

Official Action for Canada Patent Application No. 2887238, dated Apr. 26, 2022, 5 pages.

Official Action for U.S. Appl. No. 14/682,250, dated Jan. 12, 2018, 6 pages. Restriction Requirement.

Official Action for U.S. Appl. No. 14/682,250, dated Apr. 5, 2018, 11 pages.

Official Action for U.S. Appl. No. 14/682,250, dated Jan. 11, 2019, 12 pages.

Official Action for U.S. Appl. No. 14/682,250, dated Jul. 3, 2019, 12 pages.

Official Action for U.S. Appl. No. 14/682,250, dated Jan. 27, 2020, 14 pages.

Official Action for U.S. Appl. No. 14/682,250, dated Jun. 17, 2021, 11 pages.

Notice of Allowance for U.S. Appl. No. 14/682,250, dated Jan. 25, 2022, 14 pages.

* cited by examiner

UPPER GARMENT WORN DURING OVERHEAD WELDING

CROSS-REFERENCE TO RELATED APPLICATIONS

This application is a continuation of U.S. patent application Ser. No. 14/682,250 entitled "UPPER GARMENT WORD DURING OVERHEAD WELDING" and filed on Apr. 9, 2015 (now U.S. Pat. No. 11,350,690), the file contents of which is expressly incorporated herein by reference in its entirety.

FIELD

This disclosure relates to protective upper garments worn by welders who are welding overhead. More particularly, the disclosure relates to an upper garment for welders that protects their head and neck, arms and upper torso while welding overhead.

BACKGROUND

Welding, commonly by electrode or stick type arc welding, produces particles of hot metal and debris that spray from the welding area as sparks and spatter. The most common injury to a welder is burns that result from the particles contacting the skin. It is therefore necessary for welders to wear protective clothing such as general fire resistant clothing, safety glasses, boots, gloves and helmets. Garments made to be worn by welders are commonly made primarily of cotton. Having intercepted the hot particles, the garments themselves are subject to damage. Synthetic fabrics are not used because they melt when exposed to extreme heat and they are flammable.

Leather is a flame-resistant material that has been used as a protective material on garments worn by welders. See for example welding jackets available from Lincoln Electric, Miller Welding or Magid. Welding jackets made of full leather are known, however, these jackets are heavy and do not breathe well. Therefore, jackets of part leather and part breathable fabric have been made. For example, jackets with leather only on the arms, or only in the arms and chest, in combination with a jacket body made of a flame-resistant fabric, are known.

It is also known to use leather in over-sleeves that are slipped on over other clothing, to provide added spark, spatter and heat resistance. The sleeves can be made completely of leather, or of a combination of leather and a flame-resistant fabric. Leather has also been used to make bibs/aprons, or to make a cape and sleeves, to protect the welder from sparks and spatter.

To protect the head of the welder, welding caps, beanies and doo rags are used. These may be made of a flame-resistant material. Welding caps include a rim or bill, to be worn sideways to protect the neck to some extent.

Welders performing overhead welding operations are positioned underneath the objects to be welded together, often sitting or lying down. As compared to welders standing erect while welding, or those welding below their bodies, persons welding overhead are subject to different patterns of spatter and spark exposure, and hence burning of their garments or their person.

There is a need in the art for a durable garment that can shield and protect the key areas of the body and garments of a welder who is welding overhead, that is, the areas that are consistently subjected to damage by sparks and spatter. In other words, there is a need in the industry for a garment that protects the head and neck, the arms, the shoulders, and areas of the upper back and upper chest, from sparks and spatter during an overhead welding operation. Preferably the garment should be lightweight and breathable.

SUMMARY

In one aspect, described herein is an upper protective garment made of one or more breathable fabrics and leather, comprising:
  a) a garment body having a dominant side and a non-dominant side, a front panel, a back panel, and a neckline;
  b) a first leather sleeve attached to the dominant side and a second sleeve attached to the non-dominant side, and
  c) a hood comprising at least one side made of leather, attached to the neckline of the garment body,
wherein the hood is sized to fit underneath a welding faceshield or helmet.

In one embodiment, one side of the hood is made of leather and the other side of the hood is made of the breathable fabric.

In one embodiment a non-dominant side of the hood is made of leather and the dominant side of the hood is made of the breathable fabric.

In one embodiment the second sleeve is made of leather.

In one embodiment a shoulder and an upper front portion and an upper back portion of the garment body contiguous with the first leather sleeve, is made of leather.

In one embodiment the first leather sleeve is the left sleeve, and the right side of the hood is made of leather. The left shoulder, left upper front portion and left upper back portion of the garment body may also be made of leather. The front panel of the garment body may reversibly open and close. The front panel may open to form a left side and a right side, and close with the right side over the left side.

In one embodiment the first leather sleeve is the right sleeve, and the left side of the hood is made of leather. The right shoulder, right upper front portion and right upper back portion of the garment body may also be made of leather. The front panel of the garment body may reversibly open and close. The front panel may open to form a left side and a right side, and close with the left side over the right side.

In another aspect, described herein is an upper garment comprising:
  a) a garment body having a front and a back;
  b) a pair of leather sleeves attached to the garment body;
  c) a hood attached to a neckline of the garment body, wherein at least one side of the hood is made of leather; and
  d) leather on one shoulder and an upper front portion and an upper back portion of the garment that is contiguous with the one shoulder.

In one embodiment both sides of the hood are made of leather.

In one embodiment the one shoulder is the left shoulder. In one embodiment the one shoulder is the right shoulder.

In one embodiment the at least one side of the hood is the right side and the one shoulder is the left shoulder. In another embodiment the at least one side of the hood is the left side, and the one shoulder is the right shoulder.

In one embodiment the front of the garment body reversibly opens and closes. In one embodiment the front opens to form a left side and a right side, and closes with the right side over the left side. In another embodiment the front closes with the left side over the right side.

DETAILED DESCRIPTION

Described herein is an upper garment to be used when welding overhead, and which protects against burns on the neck and face, as well as on the arms and parts of the upper torso including shoulders, upper back and upper chest. Leather is positioned in strategic areas on the garment to protect the welder from burns, to protect the welder from the environment and to prolong the garment's service life.

In most welding operations, sparks and spatter of hot metal particles will spray from the work area against or onto the welder performing the operation. Most often, sparks and spatter that hit the welder will simply bounce off of the welder's garments and be harmless. However, given the quantity of sparks and spatter emitted, a few particles will invariably land in folds and crevices in the garments, where they can sit and smolder, causing damage to the garment and sometimes burning through the garment to burn the welder's skin. Any areas of exposed skin, for example around necklines, may also be burned by sparks and spatter that find their way to these regions.

An important rule for welding garments is to avoid synthetic fabrics, since sparks or spatter that land on a synthetic fabric may catch fire and burn quickly. Non-synthetic fabrics, such as cotton and leather (sometimes blended with a small amount of synthetic fibre) are therefore commonly used in these types of garments, and they may further be treated to be flame-resistant. The difference between a flame-resistant fabric and one that is not flame-resistant is that the flame-resistant fabric will self-extinguish upon the removal of the ignition source, whereas the non-flame-resistant garment will continue to burn. Both may be damaged by sparks and spatter that sit and smolder on the fabric.

In the welding industry, both flame-resistant and non-flame resistant fabrics are used to make garments for welders, different garments being worn depending on the Hazard Risk Category associated with the specific job task. For example, on a live pipeline project at least some of the infrastructure is already in place and there could be live product (e.g., hydrocarbons) moving through the pipe. Flame-resistant garments are often required to be worn. Greenfield pipeline projects on the other hand are new sites being developed, and there is no product moving through the pipe. Flame-resistant garments are typically not mandatory, but may be required by a site operator or specific regulatory requirements.

Figure 1A:
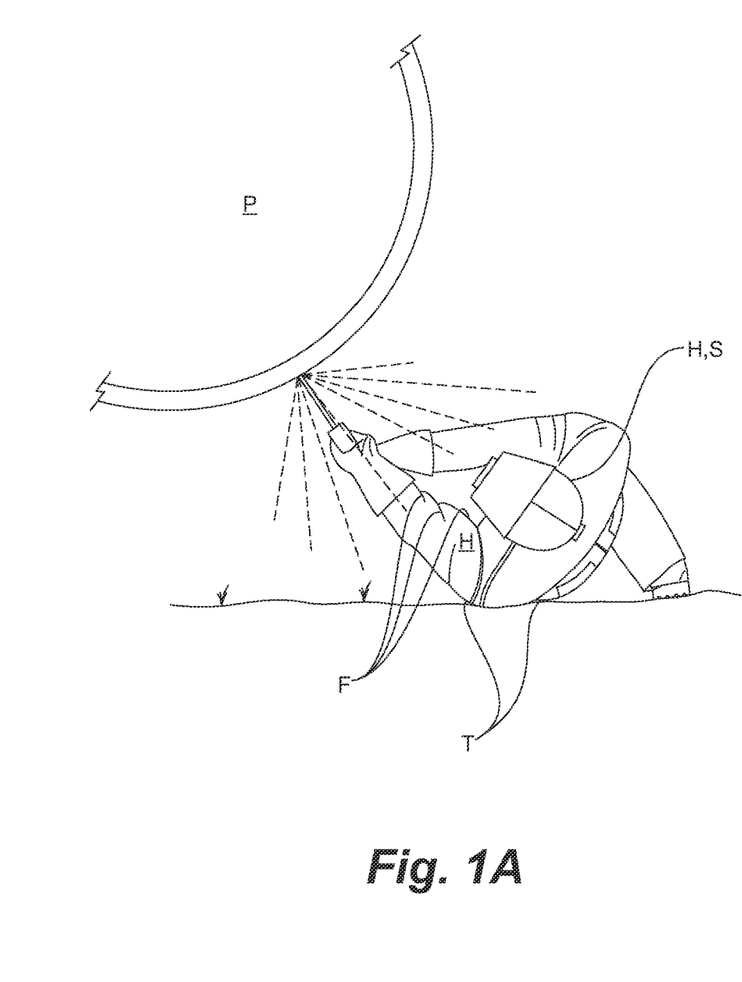
FIG. 1A is a perspective view of a left-handed welder welding a pipeline overhead.
Figure 1B:
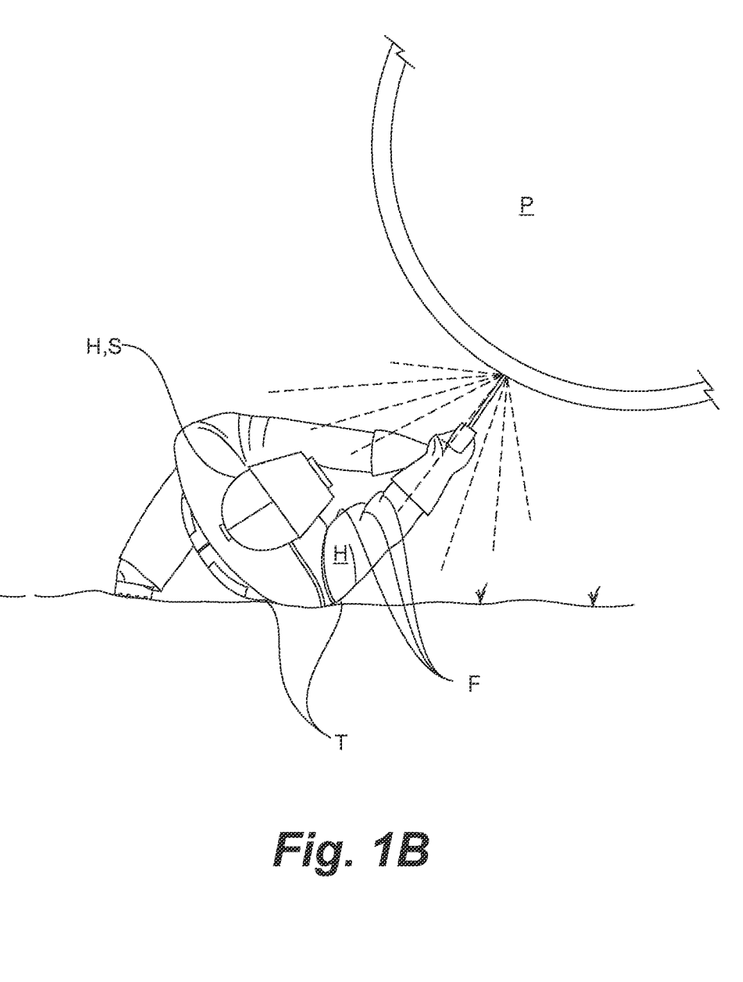
FIG. 1B is a perspective view of a right-handed welder welding a pipeline overhead.
Figure 2:
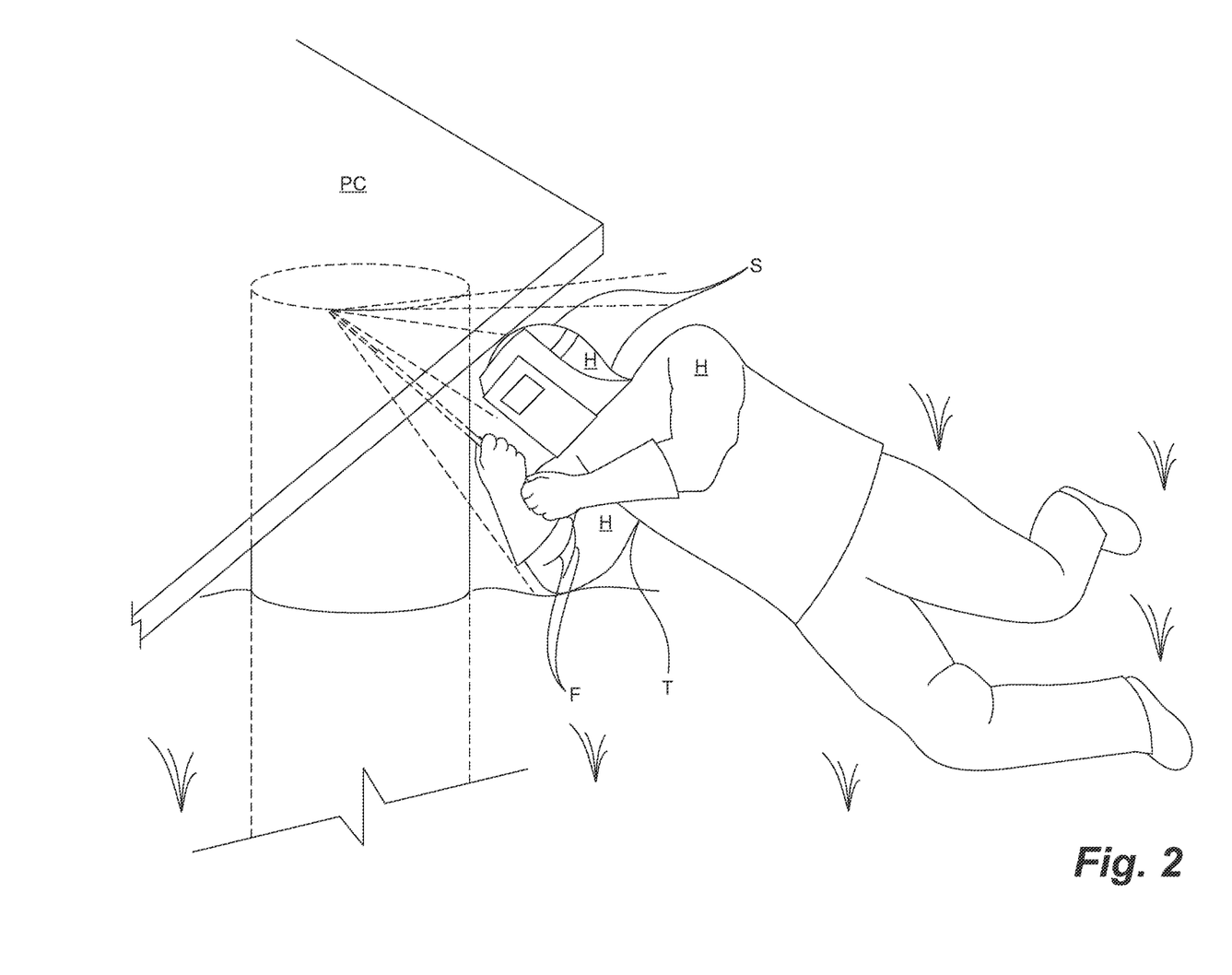
FIG. 2 is a perspective view of a welder welding underneath a pile cap.
Figure 3A:
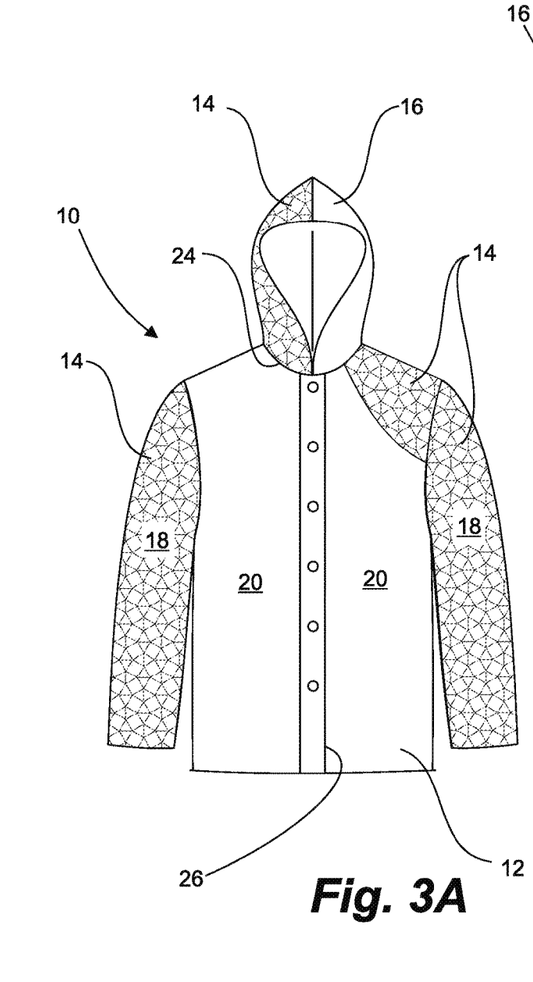
FIGS. 3A and 3B are front- and back-elevation views, respectively, of an embodiment of the upper garment for use by a left-hand dominant welder.
Figures 3B, 3C:
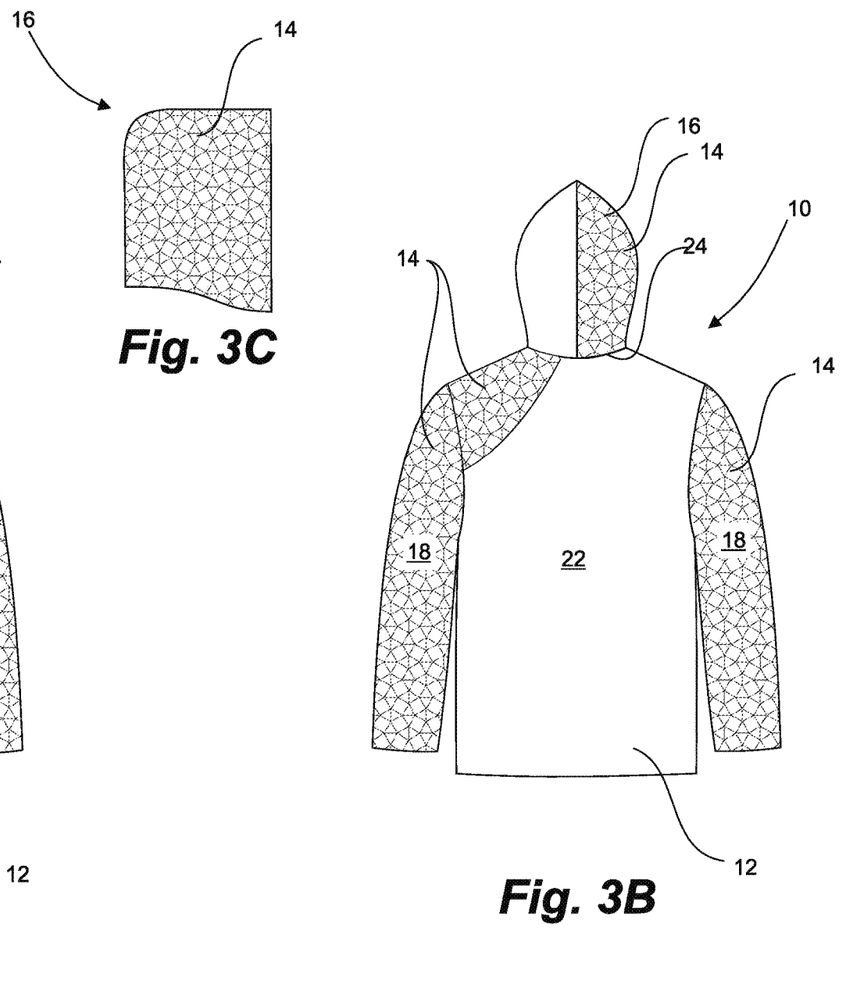
FIG. 3C is a side view of the hood of this embodiment.
Figures 4A, 4B, 4C:
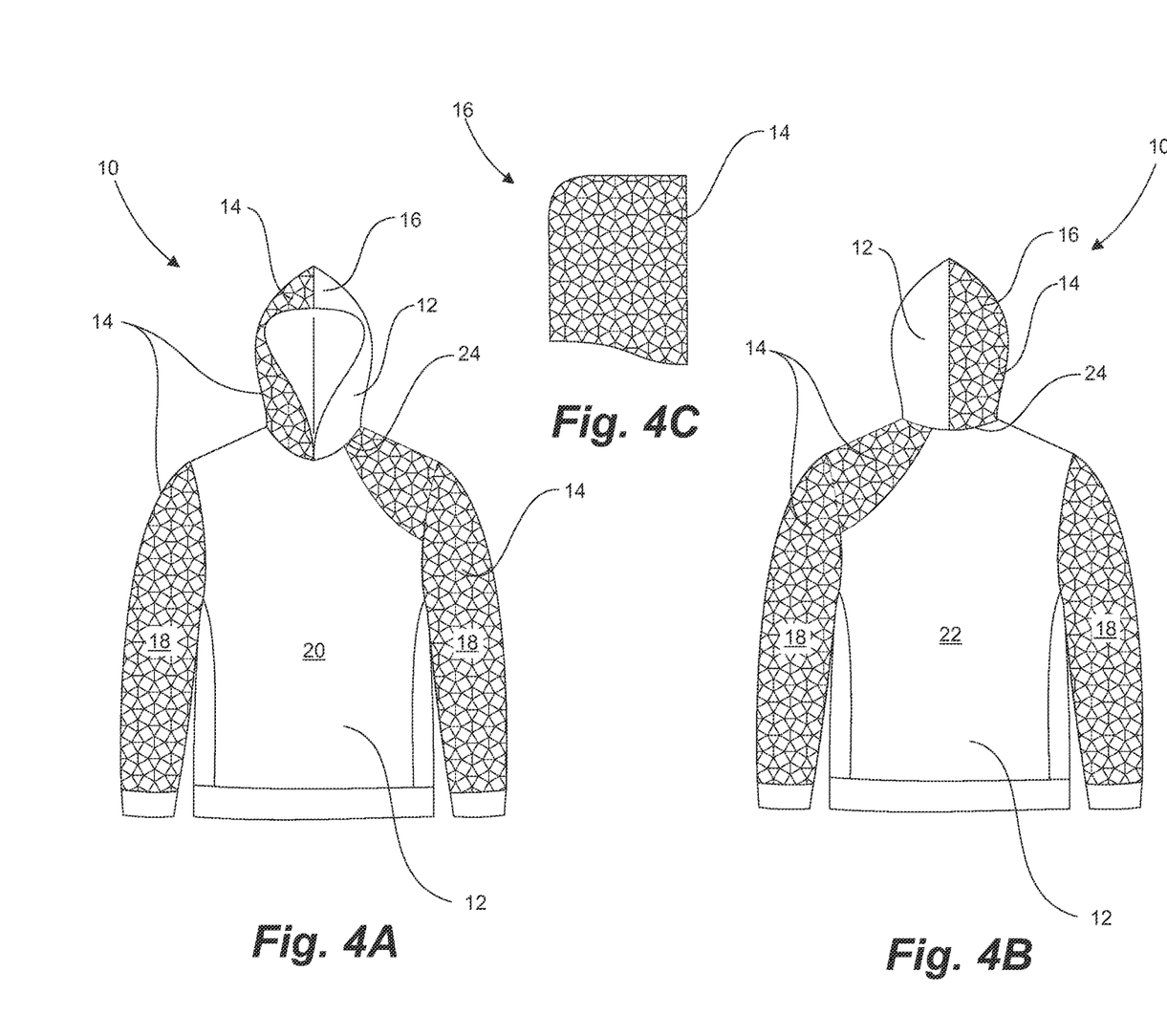
FIGS. 4A and 4B are front- and back-elevation views respectively, of an embodiment of the upper garment for use by a left-hand dominant welder.
FIG. 4C is a side view of the hood of this embodiment.

Welders performing overhead welding operations are positioned underneath the objects to be welded together, often in a sitting- or lying-down position. FIGS. 1 and 2 show two common overhead welding operations: FIG. 1 is a welder working on the ground (G) underneath a pipeline (P) and FIG. 2 is a welder working on the ground (G) underneath a pile cap (PC). While most sparks and spatter emitting from the work area will merely bounce off the welder's garments and protective shielding, given the quantity of particles a certain portion will invariably hit exposed skin that is not covered by a garment (S), will settle on generally horizontal areas of the garments (H), will settle or become trapped in the folds of the garments (F), or will accumulate between the ground and welder at areas where the particles become trapped (T). The opportunity for settled and trapped hot particles is accentuated for welders in the near-prone or prone position. Any place where hot particles rest is a place where hot particles can sit and smolder, potentially causing damage to the garment or injuring the welder.

Not-surprisingly, handedness affects the exposure of the welder's dominant side to spark and splatter damage. Surprisingly, the exposure of the welder's head is opposite to the welder's dominant side. As shown in FIG. 1A, a right-hand dominant welder working underneath the site to be welded will often weld with their right shoulder on the ground, their body positioned offset from the workpiece. The welder directs their line of site to the workpiece, and may also steady their dominant right-hand with their left-hand, both of which skew the body, causing the left side of their head (the non-dominant side of the head) to be uppermost. For a left-hand dominant welder, shown in a mirror image in FIG. 1B as a visual aid, the left side of the body and right side of the head (the non-dominant side of the head) are most at risk.

A welder performing overhead welding operations, particularly when sitting or lying on the ground is subjected to significantly different patterns of spark and spatter deposition, as compared to those standing erect while welding, or those welding below their bodies. A particular problem area for welders who are welding overhead, not experienced as much by other welders, is the burning of the head and neck where skin is often exposed. A second particular problem area for welders who are welding overhead and working on the ground is the area where sparks and spatter become trapped between the ground and welder, often between the shoulder/back and the ground. A third particular problem area for welders who are welding overhead and working on the ground is that lying or sitting on the ground underneath the area being welded is the presentation of a large surface area which results in the deposition of a larger quantity of sparks and spatter being captured either onto, or in folds of, the garment being worn.

The instant disclosure provides an upper garment to be worn by welders while welding overhead, which avoids damage to the head and neck area, and which uses leather to reinforce areas of the garment that are commonly subjected to damage from the overhead welding operation, and from environmental stresses that the garment may be subjected to while in use. For example, a welder welding overhead commonly has to lie on one side on the ground to get underneath objects that need to be welded together. Covering the dominant arm shoulder and upper back (the areas which contact the ground) with leather prolongs the life of the garment. The remainder of the garment not covered by leather is made from a breathable fabric, to reduce weight and improve the transfer of vapour and heat away from the wearer's body.

Thus the objectives of the placement of the leather on the garment are to improve the garment's durability, to minimize burns on the wearer from sparks and spatter, and to protect the garment from the environment. Another objective of the strategic placement of the leather is to maximize the breathability of the garment, that is, to minimize the total amount of leather that is used in the garment.

"Upper garment" as used herein includes a garment that a welder would wear on their upper torso between and about their shoulders and their waist, and that comprises two full-length sleeves extending from about the shoulders to the wrists. Garments such as jackets, jerseys and sweatshirts are upper garments included herein. In some embodiments the upper garment is comprised of two or more parts which when combined together form the upper garment, for example, a first part that is a vest with a hood (i.e., absent sleeves) and a second part that comprises the two sleeves.

The upper garment 10 disclosed herein may be, for example, a jacket which is put onto the wearer's body while open, and closed with buttons, a zipper, or snaps. Metal parts of the jacket such as snaps, buttons or zippers would be made with non-arcing metals. It may also be, for example, a sweatshirt-style garment that can be pulled over the head of the wearer to put it on. Other non-limiting examples of upper garments are a jersey, a shirt, a blouse, a coat, and a sweater.

The upper garment 10 described herein is comprised of a combination of a breathable fabric 12 and leather 14. The leather 14 is on the outer surface of parts of the garment, and in the embodiments shown in FIGS. 3A to 5B is indicated by the parts of the garment that are patterned. As shown in FIGS. 3A to 5B, the upper garment 10 comprises a hood 16, a pair of sleeves 18, and a front panel(s) 20 and back panel 22 in an opposing relationship.

The main component of upper garment 10 is a breathable fabric, which forms the bulk of the front panel(s) 20 and back panel 22 of the garment. In preferred embodiments, the breathable fabric lines the leather on the hood 16, the sleeves 18, and the leather on the shoulder, and upper front and upper back parts of the garment. However, this is not always the case, and in other embodiments the leather components are not lined with the breathable fabric. In a preferred embodiment, required for certification of the upper garment as a flame-resistant garment, the entirety of the upper garment is constructed of a flame-resistant breathable fabric and leather is positioned in the key areas over this flame-resistant fabric. However, if certification of the upper garment is not an objective, all or some of the leather parts need not be lined with a flame-resistant fabric. The upper garment need not have the same breathable fabric in all parts. Thus, for example, the front and back panels may be made of a flame-resistant breathable fabric, and the leather parts may be lined with a breathable fabric that is not flame-resistant.

Non-limiting examples of a breathable fabric are twill, basketweave, denim, duck cloth, or another fabric that is suitable for use in upper garments intended to be worn by welders. Preferred is a fabric that has a weight of 9 oz. (305 g/m$^2$) or greater. In some embodiments the breathable fabric is a flame-resistant fabric and it may, as well, protect from electric arc flash, flash fire, molten ferrous metal and other welding exposures. In some embodiments the breathable fabric is not flame resistant. In preferred embodiments the breathable fabric is Westex® ultrasoft® flame-resistant fabric, or Westex® ultrasoft® flame-resistant fleece. In the embodiment shown in FIGS. 4A and 4B, which is a sweatshirt-type garment, Westex® flame-resistant ribbing may be used.

Importantly, the upper garment 10 includes a hood 16 that is attached along its bottom edge to the main body of the upper garment. Hood 16 is connected to the neckline 24 of the upper garment, which is formed by the continuous top edges of the front panel(s) 20 and back panel 22 of the garment. The connection of the bottom edge of the hood with the neckline 24 of the garment is continuous over the entire length of the bottom edge of the hood, so that sparks and spatter cannot penetrate through to the inside of the garment at any point along this connection. Hood 16 may be reversibly connected to the neckline, for example by Velcro® or a zipper, however preferably it is permanently attached to the neckline by stitching. Hood 16, because it is a continuous barrier extending upwards from the neckline of the upper garment to cover the entire head, protects the head and or neck of the wearer from sparks and spatter that would hit these areas if they were exposed.

Known welding jackets do not include an attached hood, and therefore leave the neck and head exposed to burning by sparks and spatter. Sparks can fall into the crevice along the neckline of the jacket and burn the wearer. The use of welding caps, beanies or doo rags cannot avoid this eventuality. The use of a hood that is continuously attached along its bottom edge to the neckline of the garment avoids this type of burning. Further, with the added protection of leather on the hood (see next), the durability of the upper garment is improved, and the wearer is better protected, than by a hood made with only a breathable fabric, from sparks and spatter that would settle in folds of the hood.

The outer surface of hood 16 is made, at least in part, of leather. The outer surface of hood 16 may be made entirely of leather, however preferred embodiments (e.g., see the FIGS. herein) about half (a side) of the outer surface of the hood comprises leather, and about the other half (the other side) of the outer surface of the hood comprises a breathable fabric. In the hood, the breathable fabric may merely be a mesh, the purpose of which is to hold the leather part of the hood in place and provide maximum breathability. The leather part of the hood may be lined with the breathable fabric for additional comfort and/or for additional flame protection if the breathable fabric is flame-resistant. The hood 16 is designed to fit underneath a welding faceshield or helmet.

Paired sleeves 18 extend from about the shoulder down to the wrist (of the wearer), as seen in FIGS. 3A to 5B. At least the dominant-hand sleeve is made of leather. The other sleeve may be made of leather, or of a breathable fabric. The sleeves may be lined for additional comfort, for example with breathable fabric and/or for additional flame protection.

Leather is used on the outer surfaces of at least the dominant-hand sleeve, and in preferred embodiments on both sleeves, because sparks and spatter routinely settle in grooves and folds of the sleeves while welding. In addition, when the welder is on the ground it is common for sparks and spatter to become trapped between the welder's arms and the ground, or between the welders arms and their torso. In sleeves that are made of a breathable fabric, these sparks and spatter could damage the fabric and/or burn through the fabric to burn the welder's skin underneath. Leather is a more durable material and thus is not burned through as readily—prolonging the garments life and avoiding burns to the welder. For cold weather climates, flexible leather is suitable so as to retain welder mobility. One suitable type of leather that remains supple at low temperatures includes cow hide treated using various deer tanning techniques.

Figure 5A:
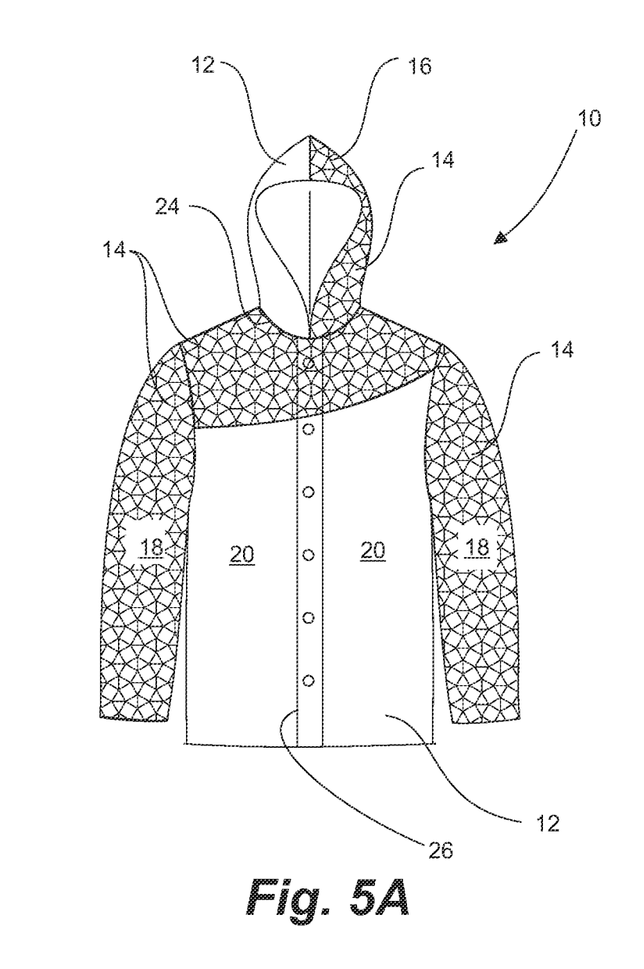
FIGS. 5A and 5B are front- and back-elevation views respectively of an embodiment of the upper garment for use by a right-hand dominant welder.
Figure 5B:
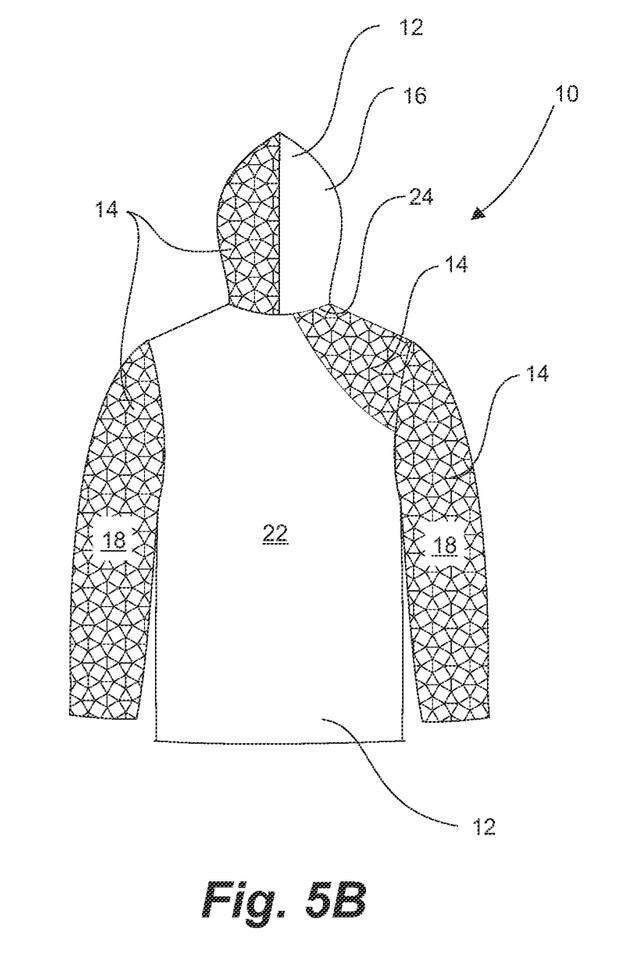

The front panel(s) 20 and back panel 22 of the upper garment together form the garment body of the jacket which envelops the torso, and comprise leather on their outer surface, at least in part. The leather parts may be lined with a breathable fabric for additional comfort and/or for additional flame protection. The areas that comprise leather are determined by which hand is dominant to the wearer of the garment. Thus, for a welder who is right-hand dominant (meaning that they hold the stinger in their right hand) leather is positioned over the right shoulder, over the right upper back area and over the right upper front area. An upper garment suitable for a right-hand dominant welder is shown in FIGS. 5A and 5B. FIGS. 3A to 4B are examples of a garment suitable for a left-hand dominant welder, with leather over the left shoulder, over the left upper back area and over the left upper front area.

Thus, in the upper garment 10 described herein, the dominant-hand shoulder (of the wearer) comprises leather on its outer surface. Leather extends from the sleeve of the dominant hand up to the neckline of the garment. The hood 16 is attached to the neckline 24 of the garment and continues on this dominant side of the body over and around the head. The hood on this dominant side may be made of leather if the hood is a complete leather hood. If not, the hood on this dominant side is made of a breathable fabric.

In addition to protecting the dominant-hand shoulder of the wearer, the leather also continues down the upper chest area and down the upper back area of the same shoulder. Optionally, the leather may also extend across to the upper chest area of the other side of the body (the non-dominant side—see FIGS. 5A and 5B). The extent of the leather on the outer surfaces of the front panel(s) 20 and back panel 22 varies depending on the types of welding activities in which the welder is engaged. Therefore, contemplated herein are upper garments that have varying degrees of protection over the upper front and upper back panels of the garment. Examples are shown in FIGS. 3A to 5B.

FIGS. 3A to 4B show embodiments of the upper garment in which the leather extends only to the upper front panel 20 and upper back panel 22 of the shoulder that is being protected, in these cases the left shoulder. As can be seen, in these embodiments the leather is wider where the shoulder joins the sleeve, and tapers towards the neck on the same side of the upper garment. This tapering is done to minimize use of leather and to maximize breathability.

FIGS. 5A and 5B show another embodiment of the upper garment, in which the leather on the upper front panel 20 of the right shoulder extends to the other (left) side of the garment as well. As shown, the leather is wider where the right shoulder joins the sleeve, and tapers towards the left shoulder. Thus, in this embodiment a larger area of protection by leather over the front of the upper garment is provided.

Leather is used on the outer surfaces of the dominant-hand shoulder and corresponding upper front and back panels because sparks and spatter routinely settle in grooves and folds of a garment in these areas, while welding overhead. In addition, when the welder is on the ground it is common for sparks and spatter to become trapped between the welder's shoulders/back and the ground. Leather therefore prolongs the garment's life and avoids burns to the wearer.

Finally, as shown in the drawings herein, the arrangement of the leather parts of the hood and shoulder are optimized for left- and right-hand dominant welders. For a right-hand dominant welder, leather is positioned on the left side of the hood, with leather over the right shoulder area. For a left-hand dominant welder, the leather is on the right side of the hood, with leather over the left shoulder area.

These areas have been determined to be most subjected to heavy sparks and spatter while welding overhead, depending on the handedness of the welder, as shown in FIGS. 1 and 2. When, for example, a right-handed welder is welding overhead and lying on the ground, the left side of the head and neck is directed upwards, and exposed to sparks and spatter from the work area. Further, their right shoulder and back are on the ground. Accordingly, an upper garment that has leather over the right shoulder/back area, and leather on the left side of the head and neck is ideal for right-handed welders working overhead. Conversely, an upper garment that has leather over the left shoulder/back area, and the right side of the head and neck is ideal for left-handed welders. The leather on the dominant-hand shoulder also functions to protect the wearer from the ground, i.e., if it is wet or muddy.

Further, on the front and back panels, 20 and 22, the leather tapers from the dominant-hand side towards the non-dominant-hand side, extending either to the neck, or beyond the neck towards or to the other shoulder. Thus, for a garment to be worn by a left-hand dominant welder, leather tapers on the upper front and upper back panels from the left shoulder to the neck, or beyond the neck towards or to the right shoulder. For a garment to be worn by a right-hand dominant welder, leather tapers on the upper front and upper back of the garment from the right shoulder to the neck, or beyond the neck towards or to the left shoulder. Again, this tapering provides the most leather in the areas where it is most needed (around the dominant-hand shoulder), and less leather where it is less needed, minimizing weight and maximizing breathability.

Because the welder is lying on the ground on either the right or left side, in garments that open and close at the front, the front panels of the garment are arranged to minimize the penetration of sparks and spatter to the inside of the garment. Thus, on a garment intended for use by right-hand dominant welder, the open edge 26 of the left front panel fastens over the open edge of the right front panel in button- or snap-closing garments (see FIG. 5A), thereby shedding sparks and spatter arriving from the left side. A zippered garment may have a flap extending along the open edge of the left front panel, to cover the zipper. Conversely, on a garment intended for use by left-hand dominant welder, the open edge 26 of the right front panel fastens over the open edge of the left front panel in button- or snap-closing garments (see FIG. 3A), shedding sparks and spatter arriving from the right side. A zippered garment may have a flap extending along the open edge of the right front panel, to cover the zipper.

Stitching on the garment may be reinforced in areas that are subjected to the heaviest wear and tear, to prolong the garment's work life. Accordingly, the edges of the leather on the front and back panels of the garment may be stitched several times, such as in 2 or more parallel lines of stitches.

Leather as used herein means a material that is created by the tanning of animal rawhide and skin. Preferred for use in the upper garment described herein, primarily for cost, is leather made from cow skin. In some embodiments, preferred for use is leather that is tanned using a process that results in a more supple leather, as this type of leather is more malleable in colder climates. For example, deer tanning of cowhide results in a leather that is suitable for use in temperatures below −10° C. Preferred for use herein is leather that is 3.0 to 3.5 oz. (1.2 to 1.4 mm thick).

While the upper garment has been described in conjunction with the disclosed embodiments, it should be understood that this is by illustration only. The scope of the claims should not be limited to the preferred embodiments but should be given the broadest interpretation consistent with the description as a whole.

The invention claimed is:

1. A protective garment for use in welding, the garment comprising:
   a) an interior surface and an exterior surface;
   b) a garment body having a first side comprising a dominant side configured to correspond to the user's dominant hand and a second side configured to correspond to the user's non-dominant hand, a front panel, a back panel, and a neckline;
   c) a first sleeve attached to the first side and a second sleeve attached to the second side, wherein the exterior surface of the first sleeve and the second sleeve comprise flame- and spatter-resistant material;
   d) a hood with a first side corresponding to the first side of the garment body and a second side corresponding to the second side of the garment body, an opening having an open perimeter and a neckline perimeter,
   wherein the hood is attached to the neckline of the garment body at the neckline perimeter of the hood,
   wherein the interior surface of the hood comprises a breathable fabric,
   wherein the first side of the hood and the second side of the hood are separated by a center dividing line extending from a front of the hood at the open perimeter to a back of the hood at the neckline perimeter, wherein the center dividing line separates the neckline perimeter into a first side corresponding with the first side of the hood and a second side corresponding with the second side of the hood, and
   e) wherein the first side of the hood is about half of the exterior surface of the hood which continuously extends from the center dividing line to the first side of the neckline perimeter and is made of breathable fabric and the second side of the hood is about half of the exterior surface of the hood which continuously extends from the center dividing line to the second side of the neckline perimeter and is made of flame- and spatter-resistant material; wherein the exterior surface of a shoulder and a first upper front portion and a first upper back portion of the garment body that are contiguous with the first sleeve are made of flame- and spatter-resistant material, and
   wherein the first side of the neckline perimeter of the hood connects to the neckline at the shoulder, the first upper front portion, and the first upper back portion of the garment body;
   f) wherein the exterior surface of a second upper back portion of the garment body that is contiguous with the second sleeve is made of breathable fabric and the exterior surface of a second upper front portion of the garment body that is contiguous with the second sleeve is made of flame- and spatter-resistant material, and
   wherein the second side of the neckline perimeter of the hood connects to the neckline at the second upper back portion and the second upper front portion of the garment body;
   g) wherein at least a portion of the exterior surface of the front panel and the back panel of the garment body are made of breathable fabric; and wherein the hood is sized to fit underneath a welding faceshield or helmet wherein, if the flame- and spatter-resistant material is a breathable fabric, it is a different breathable fabric from the breathable fabric.

2. The garment of claim 1, wherein the first sleeve is a right sleeve, and the second side of the hood is a left side of the hood and is made of flame- and spatter-resistant material.

3. The garment of claim 2, wherein the shoulder is a right shoulder, the first upper front portion is a right upper front portion and the first upper back portion is a right upper back portion.

4. The garment of claim 3, wherein the front panel of the garment body reversibly opens and closes.

5. The garment of claim 4, wherein the front panel opens to separate the first side and the second side and closes with the left side over the right side.

6. The protective garment of claim 1, wherein the flame- and spatter-resistant material on the first upper front portion of the garment extends to and is contiguous with the second sleeve.

7. The garment of claim 1 wherein the front panel of the garment body reversibly opens and closes.

8. The garment of claim 7, wherein the front panel opens to separate the first side and the second side and closes with the second side over the first side.

9. The garment of claim 1, wherein the flame- and spatter-resistant material is leather.

10. A welding garment made of one or more breathable fabrics and flame- and spatter-resistant material comprising:
    an exterior and an interior,
    a garment body having a front and a back, a first side configured to correspond to the user's dominant hand and a second side configured to correspond to the user's non-dominant hand;
    a first sleeve of flame- and spatter-resistant material attached to the first side of the garment body and a second sleeve of flame- and spatter-resistant material attached to the second side of the garment body;
    a hood attached to a neckline of the garment body at a perimeter of the hood, the hood having a center dividing line on the exterior extending from a front opening of the hood to a back of the hood, the center dividing line dividing the hood into a first side and a second side and dividing the perimeter into a first side corresponding to the first side of the hood and a second side corresponding to the second lateral side of the hood, wherein the exterior of the second side of the hood is made of flame- and spatter-resistant material which continuously extends from the center dividing line to the second side of the perimeter, and wherein the exterior of the first side of the hood is made of breathable fabric which continuously extends from the center dividing line to the first side of the perimeter;
    wherein the exterior of a shoulder, an upper front portion, and an upper back portion of the first side of the garment body is made of flame- and spatter-resistant material;
    wherein the shoulder, the upper front portion, and the upper back portion of the first side of the garment body connect to the hood at the first side of the perimeter;
    wherein the exterior of an upper back portion of the second side of the garment body is made of breathable fabric and the exterior of an upper front portion of the second side of the garment body is made of flame- and spatter-resistant material;

wherein the upper back portion and the upper front portion of the second lateral side of the garment body connect to the hood at the second side of the perimeter; and wherein at least a portion of the exterior of the front and back of the garment is made of the one or more breathable fabric wherein, if the flame- and spatter-resistant material is a breathable fabric, it is a different breathable fabric from the one or more breathable fabric.

11. The garment of claim 10, wherein the second side of the hood is a left side, and wherein the shoulder is a right shoulder.

12. The garment of claim 11, wherein the front of the garment reversibly opens and closes.

13. The garment of claim 12, wherein the front opens to form a left side and a right side, and closes with the left side over the right side.

14. The protective garment of claim 10, wherein the flame- and spatter-resistant material on the upper front portion of the garment extends to and is contiguous with the second sleeve.

15. The garment of claim 10, wherein the first and second sides of the hood each comprises about half of the hood.

16. The garment of claim 10, wherein the flame- and spatter-resistant material is leather.

\* \* \* \* \*